United States Patent
Durmaz et al.

(10) Patent No.: US 7,169,911 B2
(45) Date of Patent: Jan. 30, 2007

(54) ABIZ PHAGE RESISTANCE GENE

(75) Inventors: Evelyn Durmaz, Raleigh, NC (US);
Todd R. Klaenhammer, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 141 days.

(21) Appl. No.: 10/651,768

(22) Filed: Aug. 29, 2003

(65) Prior Publication Data
US 2005/0130126 A1    Jun. 16, 2005

Related U.S. Application Data

(60) Provisional application No. 60/407,556, filed on Aug. 30, 2002.

(51) Int. Cl.
| C12N 15/31 | (2006.01) |
| C12N 15/74 | (2006.01) |
| C12N 1/21  | (2006.01) |
| A23C 9/12  | (2006.01) |

(52) U.S. Cl. .................. 536/23.1; 536/23.7; 435/252.9; 435/320.1; 426/34; 426/43

(58) Field of Classification Search ............. None
See application file for complete search history.

(56) References Cited

U.S. PATENT DOCUMENTS

| 4,931,396 A * | 6/1990 | Klaenhammer et al. . 435/252.3 |
| 5,139,950 A | 8/1992 | Klaenhammer et al. |
| 5,538,864 A | 7/1996 | Hill et al. |
| 5,593,885 A | 1/1997 | Klaenhammer et al. |
| 5,618,723 A | 4/1997 | Klaenhammer et al. |
| 5,792,625 A | 8/1998 | Klaenhammer et al. |
| 6,242,194 B1 | 6/2001 | Kullen et al. |

OTHER PUBLICATIONS

Altschul et al.; Basic Local Alignment Search Tool, *J. Mol. Biol.*, 215:403-410 (1990).
Altschul et al., Gapped BLAST and PSI-BLAST: a new generation of protein database search programs, *Nucleic Acids Research*, vol. 25, No. 17:3389-3402 (1997).
Dinsmore, P.K., et al., "Characterization of a Genomic Region in a *Lactococcus* Bacteriophage That is Involved in Its Sensitivity to the Phage Defense Mechanism AbiA†," *Journal of Bacteriology*, 1997, pp. 2949-2957, vol. 179(9).

(Continued)

*Primary Examiner*—Kathleen M. Kerr
*Assistant Examiner*—William W. Moore
(74) *Attorney, Agent, or Firm*—Alston & Bird LLP (57) ABSTRACT

A first aspect of the present invention is an isolated nucleic acid encoding a phage abortive defense protein, the isolated nucleic acid selected from the group consisting of: (a) isolated nucleic acid having the sequence or coding sequence given in SEQ ID NO: 1 (by "coding sequence" is meant nucleotides 373 to 1668 therein); (b) isolated nucleic acid encoding a phage abortive defense protein and which hybridizes to an nucleic acid having the sequence or coding sequence given in SEQ ID NO: 1, and/or having a sequence at least 60, 70, 80, 90, 92 or 95 percent identical to the sequence or coding sequence given in SEQ ID NO: 1; and (c) isolated nucleic acid encoding a phage abortive defense protein encoded by an isolated nucleic acid of (a) or (b) above, but differing in sequence therefrom due to the degeneracy of the genetic code (e.g., a nucleic acid encoding the protein given in SEQ ID NO: 2).

24 Claims, 8 Drawing Sheets

OTHER PUBLICATIONS

Durmaz, E., et al., "Molecular Characterization of a Second Abortive Phage Resistance Gene Present in *Lactococcus lactis* subsp. *lactis* ME2†," *Journal of Bacteriology*, 1992, pp. 7463-7469, vol. 174(22).

Higgins, D.L., et al., "Restriction and Modification Activities from *Streptococcus lastis* ME2 are Encoded by a Self-Transmissible Plasmid, pTN20, that Forms Cointegrates During Mobilization of Lactose-Fermenting Ability†," *Journal of Bacteriology*, 1998, pp. 3435-3442, vol. 170(8).

Hill, C., et al, "Nucleotide Sequence and Distribution of the pTR2030 Resistance Determinant (hsp) Which Aborts Bacteriophage Infection in *Lactococci†*," *Applied and Environmental Microbiology*, 1990, pp. 2255-2258, vol. 56(7).

Hill, C., et al., "The Conjugative Plasmid pTR2030 Encodes Two Bacteriophage Defense Mechanisms in *Lactococci*, Restriction Modification ($R^+/M^+$) and Abortive Infection $(Hsp)^+$ †," *Applied and Environmental Microbiology*, 1989, pp. 2416-2419, vol. 55(9).

Hill, C., et al., "Localization, Cloning, and Expression of Genetic Determinants for Bacteriophage Resistance (Hsp) from the Conjugative Plasmid pTR2030†," *Applied and Environmental Microbiology*, 1989, pp. 1684-1689, vol. 55(7).

Klaenhammer, T.R., et al., "Molecular Analysis of pTR2030 Gene systems That Confer Bacteriophage Resistance to *Lactococci†*," *Applied and Environmental Microbiology*, 1991, pp. 124-130.

O'Sullivan, D.J., et al., "In vivo Restriction by *LlaI* is Encoded by Three Genes, Arranged in an Operon with *IIaIM*, on the Conjugative *Lactococcus* Plasmid pTR2030†," *Journal of Bacteriology*, 1995, pp. 134-143, vol. 177(1).

Romero, D.A., et al., "Abortive Phage Infection and Restriction/Modification Activities Directed by pTR2030 Determinants are Enhanced by Recombination with Conjugal Elements in *Lactococci*," *Journal of General Microbiology*, 1990, pp. 1817-1824, vol. 136.

Romero, D.A., et al., "Characterization of Insertion Sequence IS946, an Iso-ISS1 Element, Isolated from the Conjugative *Lactococcal* Plasmid pTR2030†," *Journal of Bacteriology*, 1990, pp. 4151-4160, vol. 172(8).

* cited by examiner

SEQUENCE LISTING

```
<160> NUMBER OF SEQ ID NOS: 2

<210> SEQ ID NO 1
<211> LENGTH: 2215
<212> TYPE: DNA
<213> ORGANISM: Lactococcus lactis
<220> FEATURE:
<221> NAME/KEY: RBS
<222> LOCATION: (356)..(361)
<220> FEATURE:
<221> NAME/KEY: gene
<222> LOCATION: (373)..(1668)
<223> OTHER INFORMATION: Abortive infection gene AbiZ
<220> FEATURE:
<221> NAME/KEY: CDS
<222> LOCATION: (373)..(1668)

<400> SEQUENCE: 1
aacgtttttc ttgagaatgc gatttaaccg atattgaaaa tactaaacag cactcatcca      60
tatgatgtcg agcatagtca gttaggctta aattccccca catatcctgc tcaacgtaat     120
cgggcgagtt gattaccatg tgcgattcaa catagcaata atcacctgcg agtacctgtt     180
cgagtaagac taggagtttg ttattttgat attaaatggt tgatctaaag ggattttagt     240
ttattagttt ttgtgaaaaa atgttatatt attttgtttg gctaccaatt tagctaccag     300
aaataaatta cttttaaaaa aatattgtat aataaaacaa agatgtaaat tgtttaggaa     360
gtgaaaaaat tt atg agt aaa gta aca gga ctt caa ata gta gtc cct aat      411
             Met Ser Lys Val Thr Gly Leu Gln Ile Val Val Pro Asn
               1               5                  10 act gag ttt atg tta aat aca ggg aat ggt gga aat tct caa agc ttt       459
Thr Glu Phe Met Leu Asn Thr Gly Asn Gly Gly Asn Ser Gln Ser Phe
    15                  20                  25 aaa tct ttg aat gaa tta ata gat att cta aga ata gcg att gtt gat       507
Lys Ser Leu Asn Glu Leu Ile Asp Ile Leu Arg Ile Ala Ile Val Asp
 30                  35                  40                  45 tgg aaa agg gcg gaa gga aga gga aag gcg gct ttt aaa ttt tct gaa       555
Trp Lys Arg Ala Glu Gly Arg Gly Lys Ala Ala Phe Lys Phe Ser Glu
                 50                  55                  60 act tac gct gaa gtt ctt gag ttt ata gaa aaa gat tta att tca ggg       603
Thr Tyr Ala Glu Val Leu Glu Phe Ile Glu Lys Asp Leu Ile Ser Gly
             65                  70                  75
```

-continued

| | | |
|---|---|---|
| att agt gaa gaa aat tta aat tca aga gaa gat tta ttt aag ttt ttt<br>Ile Ser Glu Glu Asn Leu Asn Ser Arg Glu Asp Leu Phe Lys Phe Phe<br>        80                              85                          90 | 651 |
| gat caa tct gtt aat aag cag gga aac tcg tgg agt ttc ata tgg caa<br>Asp Gln Ser Val Asn Lys Gln Gly Asn Ser Trp Ser Phe Ile Trp Gln<br>95                            100                        105 | 699 |
| tac tct tac agt aat tat cat cct act ttt gat att caa cct cct cta<br>Tyr Ser Tyr Ser Asn Tyr His Pro Thr Phe Asp Ile Gln Pro Pro Leu<br>110                        115                      120                  125 | 747 |
| tta tcg gag gta aat gga gat aat tat aag gct ggt tat aag att tta<br>Leu Ser Glu Val Asn Gly Asp Asn Tyr Lys Ala Gly Tyr Lys Ile Leu<br>                130                      135                      140 | 795 |
| aaa aat acc tct gtt gaa gct tat agg gaa ttt ttt gaa cta ttt aga<br>Lys Asn Thr Ser Val Glu Ala Tyr Arg Glu Phe Phe Glu Leu Phe Arg<br>            145                      150                      155 | 843 |
| aat agt ggt cag tta att aat aat ctt aac tcc agt aat aaa gca aaa<br>Asn Ser Gly Gln Leu Ile Asn Asn Leu Asn Ser Ser Asn Lys Ala Lys<br>        160                      165                      170 | 891 |
| att gaa gga tca ctt gca ttt ctg tct atc aag gtt cag aat aag gct<br>Ile Glu Gly Ser Leu Ala Phe Leu Ser Ile Lys Val Gln Asn Lys Ala<br>175                        180                      185 | 939 |
| att ctt gga tta aat act aat ctt gat gaa aaa gga gca gat cta att<br>Ile Leu Gly Leu Asn Thr Asn Leu Asp Glu Lys Gly Ala Asp Leu Ile<br>190                        195                      200                  205 | 987 |
| gta aag atg agt caa gtc tct tca tct att gac tct gca aga gta tca<br>Val Lys Met Ser Gln Val Ser Ser Ser Ile Asp Ser Ala Arg Val Ser<br>                210                      215                      220 | 1035 |
| ttt gaa gac gaa act caa aaa tat tta gag gca caa aaa gat cgg ttt<br>Phe Glu Asp Glu Thr Gln Lys Tyr Leu Glu Ala Gln Lys Asp Arg Phe<br>            225                      230                      235 | 1083 |
| gaa aaa gca gat gcg gaa cat gtt att tat att gag gaa tta aaa gat<br>Glu Lys Ala Asp Ala Glu His Val Ile Tyr Ile Glu Glu Leu Lys Asp<br>        240                      245                      250 | 1131 |
| aat ctt act gat ttt atc aaa gaa aaa aga gaa cag ttt tca aat ctc<br>Asn Leu Thr Asp Phe Ile Lys Glu Lys Arg Glu Gln Phe Ser Asn Leu<br>255                        260                      265 | 1179 |
| gaa gat tct tat gag caa aaa ttg aag tta aaa gct ccg ata aaa ttc<br>Glu Asp Ser Tyr Glu Gln Lys Leu Lys Leu Lys Ala Pro Ile Lys Phe<br>270                        275                      280                  285 | 1227 |
| tgg gaa gat gaa gca aaa aaa tat aaa atg agt gca ata tat tgg tca<br>Trp Glu Asp Glu Ala Lys Lys Tyr Lys Met Ser Ala Ile Tyr Trp Ser<br>                290                      295                      300 | 1275 |
| gta gga gcg gtt att tca gga tta tta ata att ttg aca ggg cta tgg<br>Val Gly Ala Val Ile Ser Gly Leu Leu Ile Ile Leu Thr Gly Leu Trp<br>            305                      310                      315 | 1323 |
| ata tta aaa ata ggt gag caa gat tta gat aag ttg aaa aat ata agc<br>Ile Leu Lys Ile Gly Glu Gln Asp Leu Asp Lys Leu Lys Asn Ile Ser<br>        320                      325                      330 | 1371 |
| ata att cct att tat ttt gtt cca att gct ctt att tct ttg ttg att<br>Ile Ile Pro Ile Tyr Phe Val Pro Ile Ala Leu Ile Ser Leu Leu Ile<br>335                        340                      345 | 1419 |
| tat atc tta aga act ttg ata aaa att gca att tct aat cag cac ata<br>Tyr Ile Leu Arg Thr Leu Ile Lys Ile Ala Ile Ser Asn Gln His Ile<br>350                        355                      360                  365 | 1467 |
| tca gta gag tac gct caa aaa gca gca tta act gat tat tat tta tct<br>Ser Val Glu Tyr Ala Gln Lys Ala Ala Leu Thr Asp Tyr Tyr Leu Ser<br>                370                      375                      380 | 1515 |
| atg att caa gaa gga cat tta ggt atc agt atc gaa gaa aaa caa tta<br>Met Ile Gln Glu Gly His Leu Gly Ile Ser Ile Glu Glu Lys Gln Leu | 1563 |

```
                    385              390              395
ctt tta cct aca atc ttt tca aaa att gat agt ggt cta att aaa tct    1611
Leu Leu Pro Thr Ile Phe Ser Lys Ile Asp Ser Gly Leu Ile Lys Ser
        400              405              410 gat tct aca gga gat tct gat att act gag tta tta aaa ata ctt gta    1659
Asp Ser Thr Gly Asp Ser Asp Ile Thr Glu Leu Leu Lys Ile Leu Val
        415              420              425 gcg aag aaa taaaatataa atattcataa tactatacaa aataacacca             1708
Ala Lys Lys
430 taagttataa cttatggtgt tattttgtat tctcgccccc tgcgacaagg gtcgagcaaa   1768 ttgctcgaat tatattaatc tctattttta aaataatctt tgagccaagt agctattatt   1828 tctttatcat tttctgtggg tttattttct ctaataatat tgaagatttc atcaaggtca   1888 ccagttcttc ctgctagata gtcaggagta acatcaagag cttttgctag tctttgtata   1948 gtggactaat gtcaaatatt tagacacaaa atgagctata ttttcttaaa ataattttct   2008 tctttctgat ttggagttaa accattgttg gcggaatgag gattataatt gttataaaat   2068 tgttcgatgt attcaaagca agagagttga acttcttgaa tggagtgata agttctgcga   2128 ttaatttctc gttgtttaag atacttgaaa aagacctcag tgacggcatt atcataagga   2188 tatccaggct tggagtaaga agcaagc                                      2215

<210> SEQ ID NO 2
<211> LENGTH: 432
<212> TYPE: PRT
<213> ORGANISM: Lactococcus lactis

<400> SEQUENCE: 2

Met Ser Lys Val Thr Gly Leu Gln Ile Val Pro Asn Thr Glu Phe
1               5                   10                  15

Met Leu Asn Thr Gly Asn Gly Asn Ser Gln Ser Phe Lys Ser Leu
                20                  25                  30

Asn Glu Leu Ile Asp Ile Leu Arg Ile Ala Ile Val Asp Trp Lys Arg
            35                  40                  45

Ala Glu Gly Arg Gly Lys Ala Ala Phe Lys Phe Ser Glu Thr Tyr Ala
    50                  55                  60

Glu Val Leu Glu Phe Ile Glu Lys Asp Leu Ile Ser Gly Ile Ser Glu
65                  70                  75                  80

Glu Asn Leu Asn Ser Arg Glu Asp Leu Phe Lys Phe Asp Gln Ser
                85                  90                  95

Val Asn Lys Gln Gly Asn Ser Trp Ser Phe Ile Trp Gln Tyr Ser Tyr
            100                 105                 110

Ser Asn Tyr His Pro Thr Phe Asp Ile Gln Pro Leu Leu Ser Glu
        115                 120                 125

Val Asn Gly Asp Asn Tyr Lys Ala Gly Tyr Lys Ile Leu Lys Asn Thr
        130                 135                 140

Ser Val Glu Ala Tyr Arg Glu Phe Phe Glu Leu Phe Arg Asn Ser Gly
145                 150                 155                 160

Gln Leu Ile Asn Asn Leu Asn Ser Ser Asn Lys Ala Lys Ile Glu Gly
                165                 170                 175

Ser Leu Ala Phe Leu Ser Ile Lys Val Gln Asn Lys Ala Ile Leu Gly
            180                 185                 190

Leu Asn Thr Asn Leu Asp Glu Lys Gly Ala Asp Leu Ile Val Lys Met
        195                 200                 205
```

-continued

```
Ser Gln Val Ser Ser Ile Asp Ser Ala Arg Val Ser Phe Glu Asp
        210             215             220

Glu Thr Gln Lys Tyr Leu Glu Ala Gln Lys Asp Arg Phe Glu Lys Ala
225             230                 235                 240

Asp Ala Glu His Val Ile Tyr Ile Glu Glu Leu Lys Asp Asn Leu Thr
            245             250                 255

Asp Phe Ile Lys Glu Lys Arg Glu Gln Phe Ser Asn Leu Glu Asp Ser
            260             265             270

Tyr Glu Gln Lys Leu Lys Leu Lys Ala Pro Ile Lys Phe Trp Glu Asp
        275             280             285

Glu Ala Lys Lys Tyr Lys Met Ser Ala Ile Tyr Trp Ser Val Gly Ala
        290             295             300

Val Ile Ser Gly Leu Leu Ile Ile Leu Thr Gly Leu Trp Ile Leu Lys
305             310             315             320

Ile Gly Glu Gln Asp Leu Asp Lys Leu Lys Asn Ile Ser Ile Ile Pro
            325             330             335

Ile Tyr Phe Val Pro Ile Ala Leu Ile Ser Leu Leu Ile Tyr Ile Leu
            340             345             350

Arg Thr Leu Ile Lys Ile Ala Ile Ser Asn Gln His Ile Ser Val Glu
        355             360             365

Tyr Ala Gln Lys Ala Ala Leu Thr Asp Tyr Tyr Leu Ser Met Ile Gln
        370             375             380

Glu Gly His Leu Gly Ile Ser Ile Glu Glu Lys Gln Leu Leu Leu Pro
385             390             395             400

Thr Ile Phe Ser Lys Ile Asp Ser Gly Leu Ile Lys Ser Asp Ser Thr
            405             410             415

Gly Asp Ser Asp Ile Thr Glu Leu Leu Lys Ile Leu Val Ala Lys Lys
            420             425             430
```

ABIZ PHAGE RESISTANCE GENE

CROSS REFERENCE TO RELATED APPLICATIONS

This application claims the benefit of, and incorporates herein by reference, the following United States Provisional Application: U.S. Provisional Application No. 60/407,556, filed Aug. 30, 2002.

FIELD OF THE INVENTION

The present invention concerns phage resistance genes, bacteria containing the same, and methods of fermentation utilizing such bacteria.

BACKGROUND OF THE INVENTION

The susceptibility of starter cultures to bacteriophage infection remains a problem in the cheese industry, especially with increasing reliance on defined starters and the high turnover in factories. Analysis of natural phage resistance mechanisms in starters has led to the identification of four categories of bacteriophage resistance in lactococci: interference with either 1) phage adsorption, or 2) phage DNA injection; 3) DNA restriction/modification (R/M); and 4) abortive infection (Abi) via a disruption of phage development post infection. Numerous plasmids encoding one or more of these systems have been isolated from commercial starter strains.

*Lactococcus lactis* ME2 is a prototype phage-resistant strain which has been used successfully in the cheese industry. ME2 contains at least three plasmids which encode distinct phage defenses. Plasmid pME0030 interferes with phage adsorption. Two self-transmissible plasmids, pTR2030 and pTN20, each encode at least one R/M system and one Abi system.

Plasmid pTR2030 has previously been partially subcloned and sequenced to reveal an R/M system, LlaI, and abortive gene, abiA.

REFERENCES

P. Dinsmore and T. Klaenhammer, *J. Bacteriol.* 179: 2949–57 (1997).

E. Durmaz et al., *J. Bacteriol.* 174: 7463–9 (1992).

D. Higgins et al., *J. Bacteriol.* 170: 3435–42 (1988).

C. Hill et al., *Appl. Environ. Microbiol.* 56: 2255–8 (1990).

C. Hill et al., *Appl. Environ. Microbiol.* 55: 2416–9 (1989).

C. Hill et al., *Appl. Environ. Microbiol.* 55: 1684–9 (1989).

T. Klaenhammer et al., Molecular analysis of pTR2030 gene systems that confer bacteriophage resistance to lactococci (1991)

D. O'Sullivan et al. *J. Bacteriol.* 177: 134–43 (1995).

D. Romero and T. Klaenhammer, *Journal of General Microbiology.* 136:1817–1824 (1990).

D. Romero and T. Klaenhammer, *J. Bacteriol.* 172: 4151–60 (1990).

SUMMARY OF THE INVENTION

A first aspect of the present invention is an isolated nucleic acid encoding a phage abortive defense protein, the isolated nucleic acid selected from the group consisting of: (a) isolated nucleic acid having the sequence or coding sequence given in SEQ ID NO: 1 (by "coding sequence" is meant nucleotides 373 to 1668 therein); (b) isolated nucleic acid encoding a phage abortive defense protein and which hybridizes to an nucleic acid having the sequence or coding sequence given in SEQ ID NO: 1, and/or having a sequence at least 60, 70, 80, 90, 92 or 95 percent identical to the sequence or coding sequence given in SEQ ID NO: 1; and (c) isolated nucleic acid encoding a phage abortive defense protein encoded by an isolated nucleic acid of (a) or (b) above, but differing in sequence therefrom due to the degeneracy of the genetic code (e.g., a nucleic acid encoding the protein given in SEQ ID NO: 2).

A second aspect of the present invention is a recombinant DNA comprising an isolated nucleic acid as described above operatively associated with a promoter. The promoter may be the native AbiZ promoter, or may be a heterologous promoter. The recombinant DNA may further comprise an AbiA gene, preferably operatively associated with a promoter. Concurrent expression of the AbiZ and AbiA genes is particularly effective in imparting phage resistance to otherwise susceptible bacteria.

A further aspect of the present invention is a recombinant plasmid containing an isolated nucleic acid as described above operatively associated with a promoter, as described above. The plasmid may further comprise or contain an AbiA gene, as described above.

A further aspect of the present invention is a method of imparting phage resistance to a bacteria, comprising: (a) providing an isolated nucleic acid as described above, the nucleic acid operatively associated with a promoter; and then (b) introducing the isolated nucleic acid into a bacteria to thereby impart phage resistance to the bacteria. As above, the bacteria may further contain an AbiA gene, on the same plasmid or vector or on a different plasmid or vector as used to carry the AbiZ gene.

A further aspect of the present invention is a bacteria produced by the methods described above, or a bacteria which contains a recombinant nucleic acid, recombinant DNA, recombinant vector or recombinant plasmid as described herein. Preferably the bacteria expresses the encoded AbiZ protein. The bacteria may further comprise or contain an AbiA gene as described above, on the same or separate plasmid or vector that contains the AbiZ gene, and preferably expresses the AbiA gene.

A further aspect of the present invention is a starter culture (e.g., for fermenting a food such as milk) comprising or consisting essentially of a Lactococcal bacteria as described above.

The present invention is explained in greater detail in the drawings herein and the specification set forth below.

DETAILED DESCRIPTION OF THE PREFERRED EMBODIMENTS

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 C.F.R §1.822 and established usage. See, e.g., Patent In User Manual, 99–102 (November 1990) (U.S. Patent and Trademark Office).

By "isolated" when referring to a nucleotide sequence, is meant that the indicated molecule is present in the substantial absence of other biological macromolecules of the same type. Thus, an "isolated nucleic acid" refers to a nucleic acid molecule which is substantially free of other nucleic acid molecules; however, the molecule may include some additional bases or moieties which do not deleteriously affect the basic characteristics of the composition.

The present invention provides nucleic acids encoding the AbiZ gene, such nucleic acids having the sequence given herein as SEQ ID NO: 1 or the coding segment thereof. Nucleic acids of the present invention also include those coding for proteins homologous to, and having essentially the same biological properties as, the protein disclosed herein (i.e., SEQ ID NO: 2). Thus, polynucleotides that hybridize to DNA disclosed herein as SEQ ID NO:1, or the coding segment thereof, or the opposite or complementary strand of either thereof, and which code on expression for a protein of the present invention (e.g., a protein according to SEQ ID NO:2), are also an aspect of the invention. Conditions which will permit other nucleic acids that code on expression for a protein of the present invention to hybridize to nucleic acids having the sequence given as SEQ ID NO:1 disclosed herein, or the coding segment thereof, can be determined in accordance with known techniques. For example, hybridization of such sequences may be carried out under conditions of reduced stringency, medium stringency or even stringent conditions (e.g., conditions represented by a wash stringency of 35–40% Formamide with 5xDenhardt's solution, 0.5% SDS and 1xSSPE at 37° C.; conditions represented by a wash stringency of 40–45% Formamide with 5xDenhardt's solution, 0.5% SDS, and 1xSSPE at 42° C.; and conditions represented by a wash stringency of 50% Formamide with 5xDenhardt's solution, 0.5% SDS and 1xSSPE at 42° C., respectively) to DNA of SEQ ID NO:1 disclosed herein in a standard hybridization assay. See, e.g., J. Sambrook et al., *Molecular Cloning, A Laboratory Manual* (2d Ed. 1989) (Cold Spring Harbor Laboratory). In general, sequences which code for proteins of the present invention and which hybridize to the DNA of SEQ ID NO:1 disclosed herein will be at least 60, 70, 75, 80, 85, 90 or 95 percent homologous or identical to SEQ ID NO:1 (or the coding segment thereof).

As is known in the art, a number of different programs can be used to identify whether a protein or nucleic acid has a given sequence identity or homology to a known sequence. Sequence identity and/or similarity is determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48, 443 (1970), by the search for similarity method of Pearson & Lipman, *Proc. Natl. Acad. Sci. USA* 85, 2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387–395 (1984), preferably using the default settings, or by inspection. Percent identity or homology may be calculated by FastDB based upon the following parameters: mismatch penalty of 1; gap penalty of 1; gap size penalty of 0.33; and joining penalty of 30, "Current Methods in Sequence Comparison and Analysis," *Macromolecule Sequencing and Synthesis,* Selected Methods and Applications, pp 127–149 (1988), Alan R. Liss, Inc.

An example of a useful algorithm for determining sequence identity or homology is the BLAST algorithm, described in Altschul et al., *J. Mol. Biol.* 215, 403–410, (1990) and Karlin et al., *Proc. Nail. A cad. Sci. USA* 90, 5873–5787 (1993). A particularly useful BLAST program is the WU-BLAST-2 program which was obtained from Altschul et al., *Methods in Enzymology*, 266, 460–480 (1996);

blast.wustl/edulblast/ README.html. WU-BLAST-2 uses several search parameters, most of which are set to the default values. The adjustable parameters are set with the following values: overlap span=1, overlap fraction=0.125, word threshold (T) =11. The HSP S and HSP S2 parameters are dynamic values and are established by the program itself depending upon the composition of the particular sequence and composition of the particular database against which the sequence of interest is being searched; however, the values may be adjusted to increase sensitivity.

Further, polynucleotides that code for proteins of the present invention, or polynucleotides that hybridize to nucleic acids having the sequence given as SEQ ID NO:1 or the coding segment therof, but which differ in codon sequence from such polynucleotides due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1.

By "recombinant nucleic acid" is meant a vector molecule that has been genetically altered, e.g., by the addition or insertion of a heterologous nucleic acid construct into the cloning vector. A "cloning vector" is a DNA molecule, such as a plasmid, cosmid, or integratable DNA fragments (i.e., fragments integratable into the host genome by recombination).

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59. (Applicant specifically intends that the disclosure of all patent references cited herein be incorporated herein in their entirety by reference).

Any suitable promoter can be used to carry out the present invention, including the native AbiZ promoter or a heterologous promoter. Heterologous promoters may be constitutively active or inducible. A non-limiting example of a heterologous promoter is given in U.S. Pat. No. 6,242,194 to Kullen and Klaenhammer.

The production of bacteria containing heterologous phage resistance genes, the preparation of starter cultures of such bacteria, and methods of fermenting substrates, particularly food substrates such as milk, may be carried out in accordance with known techniques, including but not limited to those described in U.S. Pat. No. 6,242,194 to Kullen and Klaenhammer; U.S. Pat. No. 5,792,625 to Klaenhammer et al.; U.S. Pat. No. 5,618,723 to Klaenhammner and Moineau; U.S. Pat. No. 5,593,885 to Klaenhammer, Sing and Hill; U.S. Pat. No. 5,538,864 to Hill and Klaenhammer; and U.S. Pat. No. 5,139,950 to Klaenhammer, Sanozky and Steenson.

Lactococcal bacteria are particularly preferred as host bacteria for carrying out the present invention. Examples of such bacteria include *Lactococcus lactis* subsp. *lactis, Lactococcus lactis* subsp. *cremoris,* and *Lactococcus lactis* subsp. *lactis biovar. diacetylactis.*

Starter cultures employed in practicing the present invention may be in any physical form, including liquid cultures of the fermentation bacteria in a suitable growth medium, as well as lyophilized cultures, immobilized cells, and frozen cultures prepared therefrom.

Starter cultures employed in the present invention are preferably defined cultures (i.e., cultures of known bacterial content). Such defined cultures may be either single strain cultures or multiple strain cultures.

Methods of using the bacteria or starter cultures of the present invention are generally carried out by providing a bacteria such as a lactococcal bacteria that contains (and preferably replicates) a heterologous nucleic acid as described above, and then combining the bacteria with a substrate such as milk under conditions that facilitate the growth of the bacteria therein to ferment the substrate. The fermentation may be carried out under sterile or nonsterile conditions, and under any suitable temperature, depending upon the bacteria and substrate employed and the particular purpose of the fermentation.

The present invention is explained in greater detail in the following non-limiting Examples.

EXAMPLE 1

Sequencing of the Region between AbiA and IS946

The region downstream of abiA was PCR-amplified using primers homologous to the C-terminal end of abiA and to IS946. ApoI and RsaI digested PCR products were separately cloned into EcoRI and EcoRV digested pZErOÆË-2. Sequencing of the random clones was done at the NCSU Genome Research Center on a Perkin Elmer Prism 3700 sequencer. Gaps between 13 contigs, obtained after assembly with Consed software, were closed using PCR products produced from the ends of the contigs. All ambiguities or single stranded regions identified by Consed were also resolved to obtain the complete double stranded sequence of the 7.5-kb region. The sequence was analyzed using Clone Manager 6.0 and NCBI Blast and ORF finder software.

EXAMPLE 2

Sequence Analysis of the 9 kb Region

Figure 1:
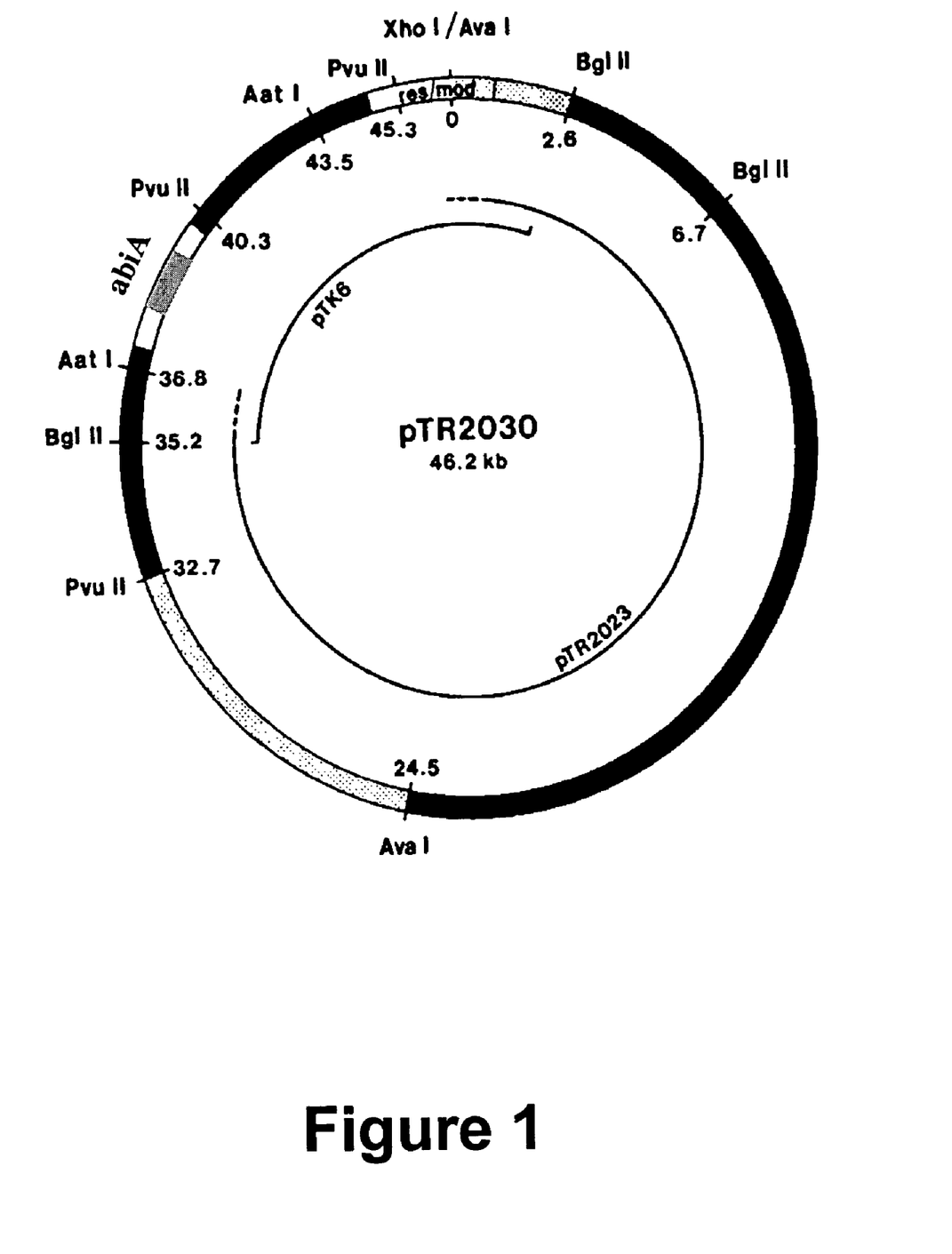
FIG. 1. Map of pTR2030. The abiA gene is indicated. Shaded regions contain IS946. Subclone pTK6 encodes LlaI and abiA. Subclone pTR2023 lacks phage resistance.
Figure 2:
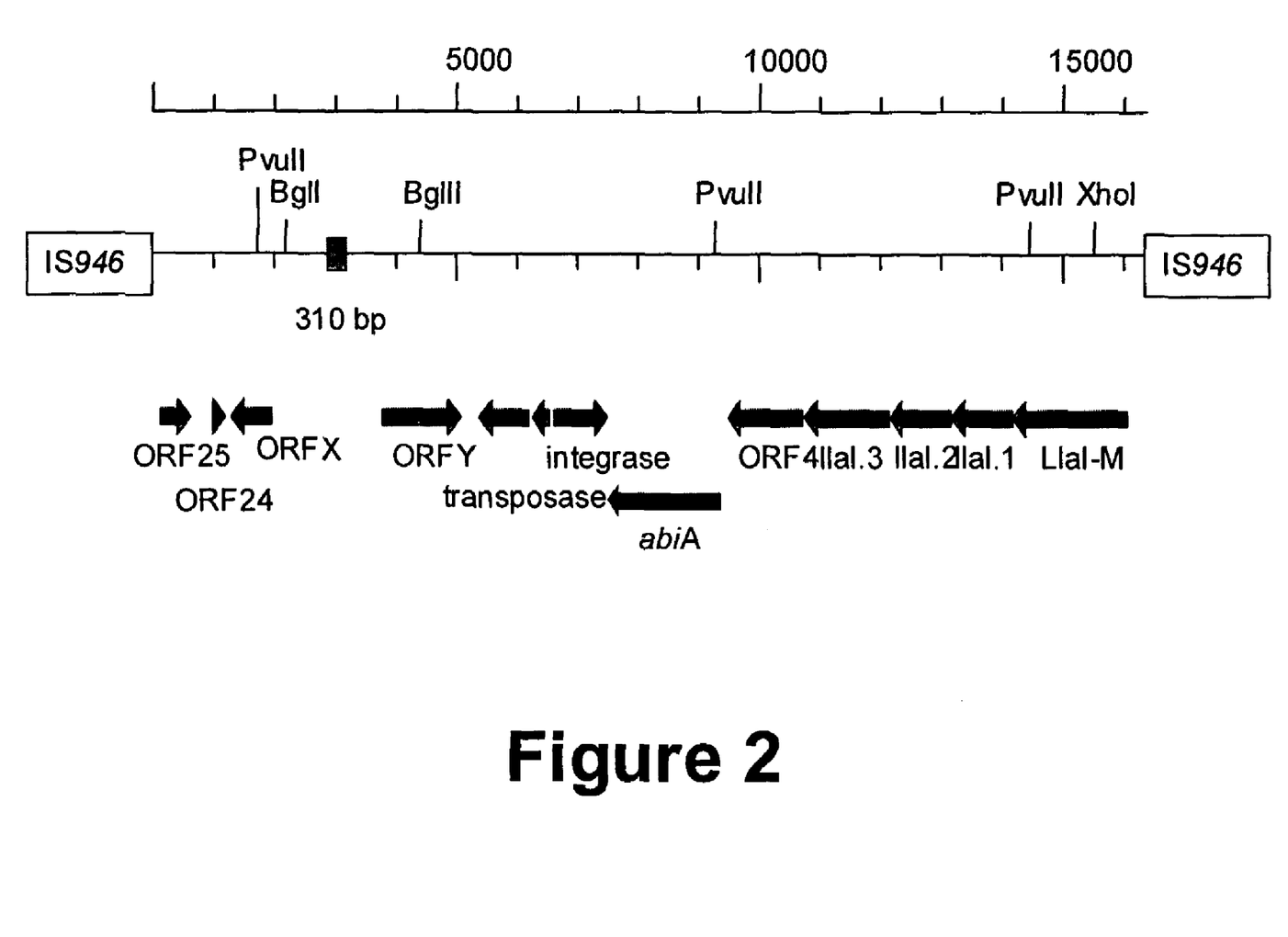
FIG. 2. Map of pTR2030 between the two copies of IS946. The previously sequenced region including the R/M region and abiA (GenBank sequence U17233) are included. Putative gene functions are indicated where amino acid homologies were found in Blast searches.
Figure 3:
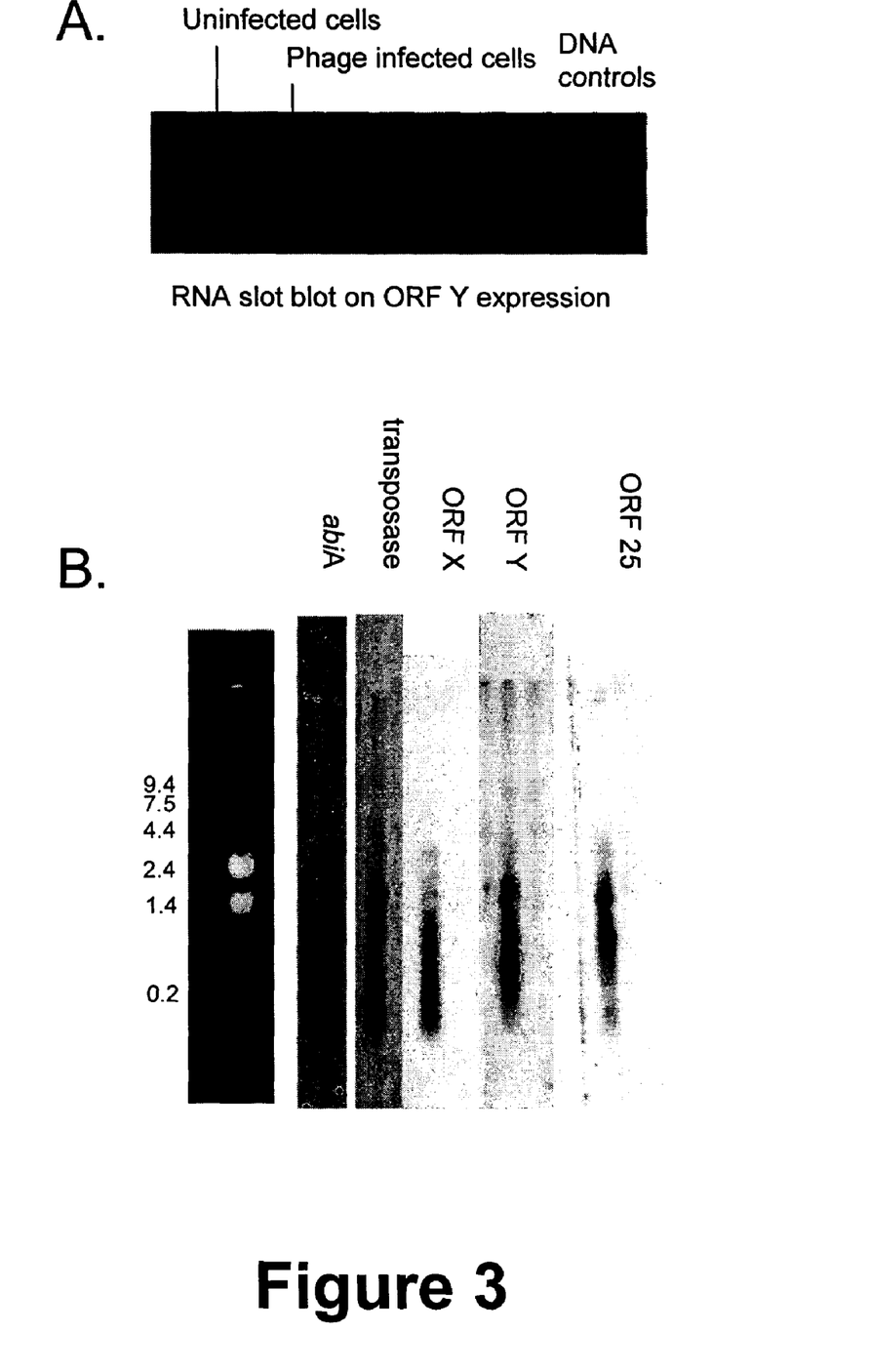
FIG. 3. A. Northern slot blot experiments with RNA probes were used to determine gene expression and relative strength of the transcripts. B. Double stranded DNA probes were used for detection of transcript lengths in the Northern experiment. C. Green bars indicate the transcripts—bar width denotes approximate strength of the transcript strength. The ORF encoding the putative integrase was not expressed under the experimental conditions (log phase cells before or 12 minutes after infection).
Figure 4:
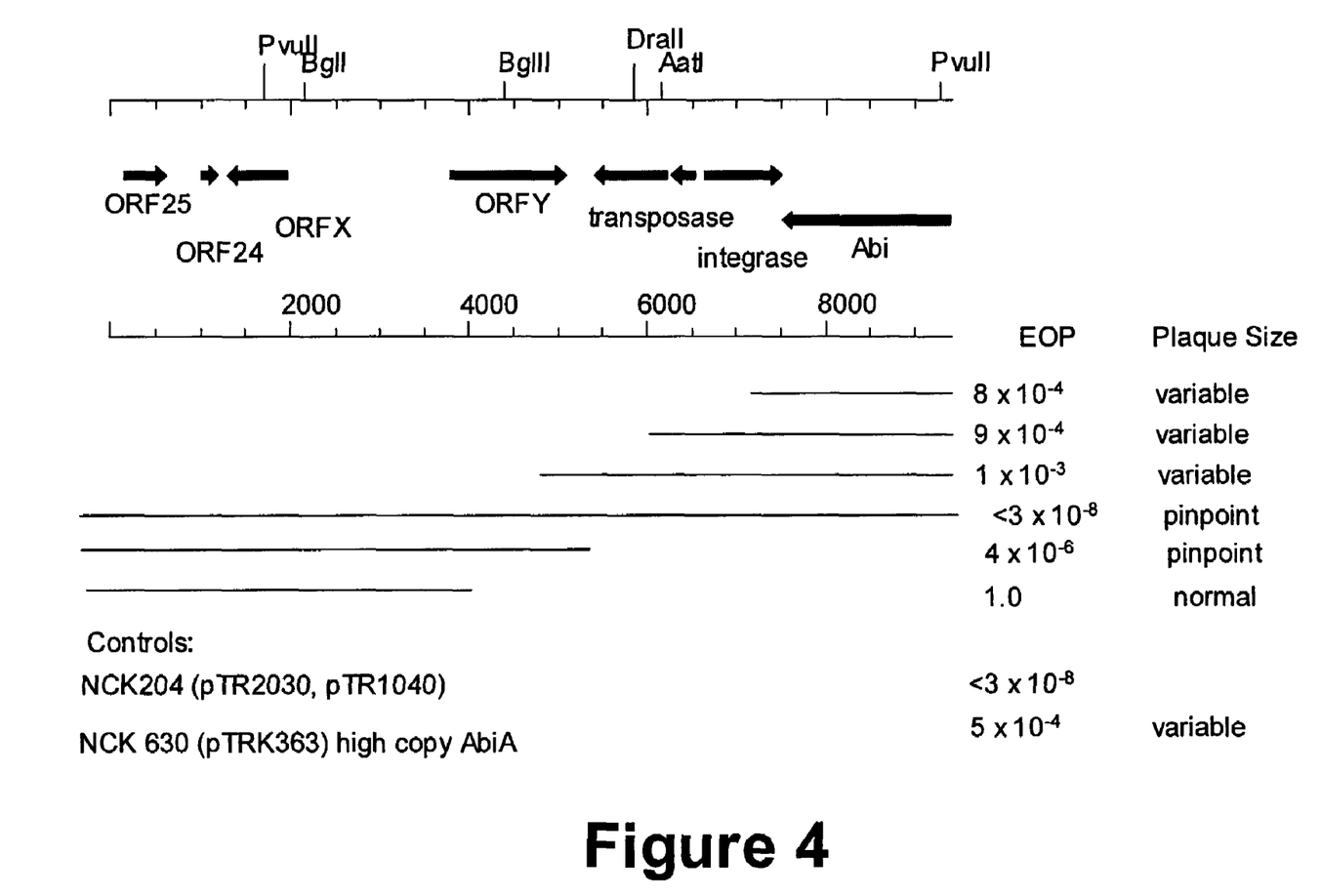
FIG. 4. Subcloning of the 9.4 kb region was accomplished by inserting PCR fragments, a BglII digested fragment, and partial EcoRV digestion products into pTRKH2. The results indicated that ORF Y was most likely responsible for the enhanced effect on phage ö31.

From left to right on the map shown in FIG. 2, the first part of the sequence is identical to sequence from the 60-kb conjugative, bacteriocin-producing plasmid pMRC01 from *Lactococcus lactis* DPC3147, and contains hypothetical ORFs 24 and 25 of that sequence. The ORF designated 25 in pMRC01 is a potential adenylate kinase (COG pet-score 13). In pTR2030, following the region of pMRC01 homology, are two hypothetical ORFs (X and Y) with no DNA or amino acid homologies. There are numerous inverted repeats (IR) located in the region between these two ORFs. A very large 46 bp IR follows ORFY. The next two ORFs comprise a putative two component transposase, followed by a putative integrase and abiA. Current analysis shows a significant alignment of abiA with the reverse transcriptase family of proteins pfam00078. The proteins most closely related to AbiA in this family are the Moloney murine leukemia virus RT, and a number of maturases associated with introns. The active domain identified in the search corresponds to the region previously identified as a leucine repeat motif. This region was essential for AbiA activity.

EXAMPLE 3

Effect of ORF Y on P335 Group Lytic Phage ö31

Figure 5:
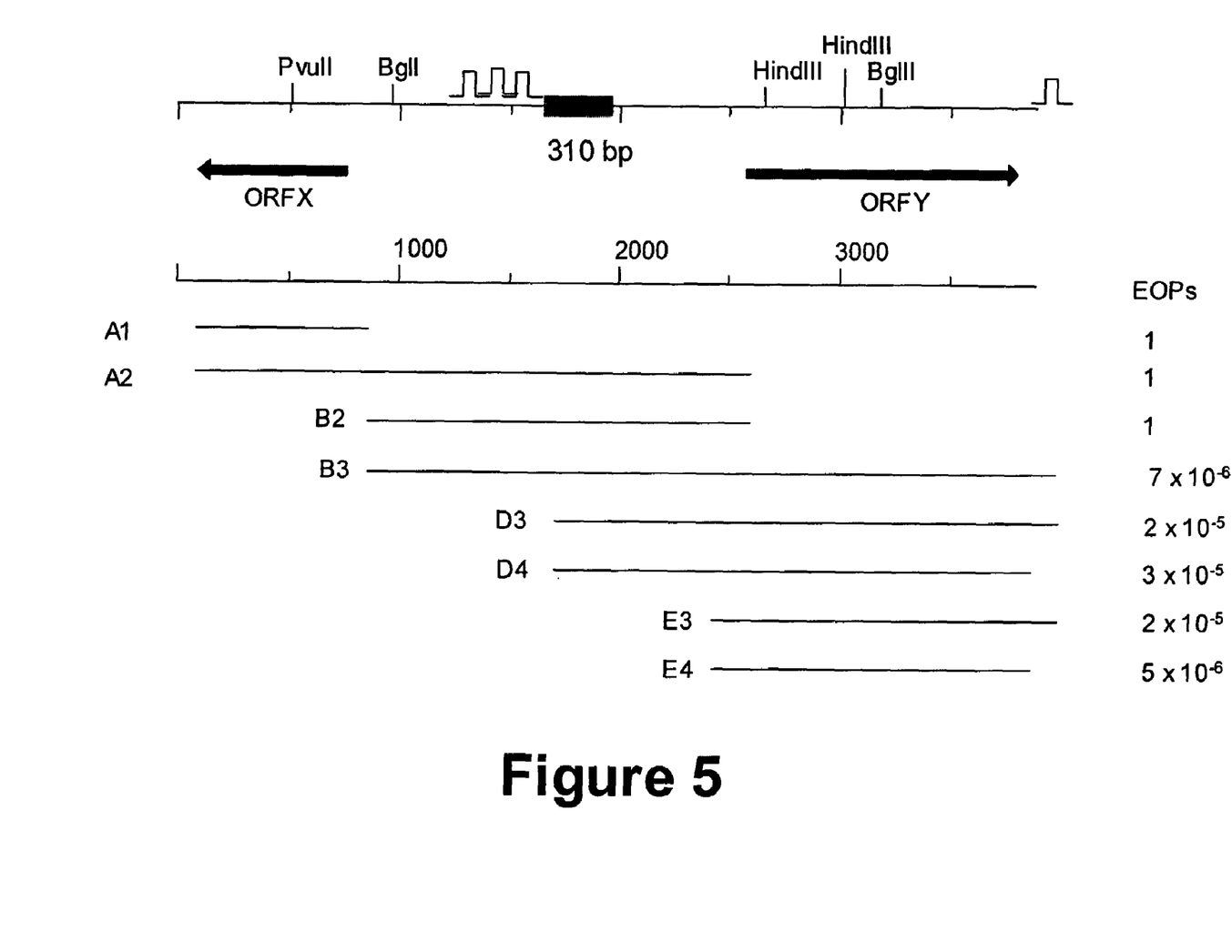
FIG. 5. Subcloning of the region containing ORFs X and Y. Symbol indicates potential stem loop structures. Boxed 310 bp region shows homology to numerous lactococcal sequenced plasmids, and occurs in the vicinity of the two component abortive determinants for AbiG and AbiL.
Figure 6:
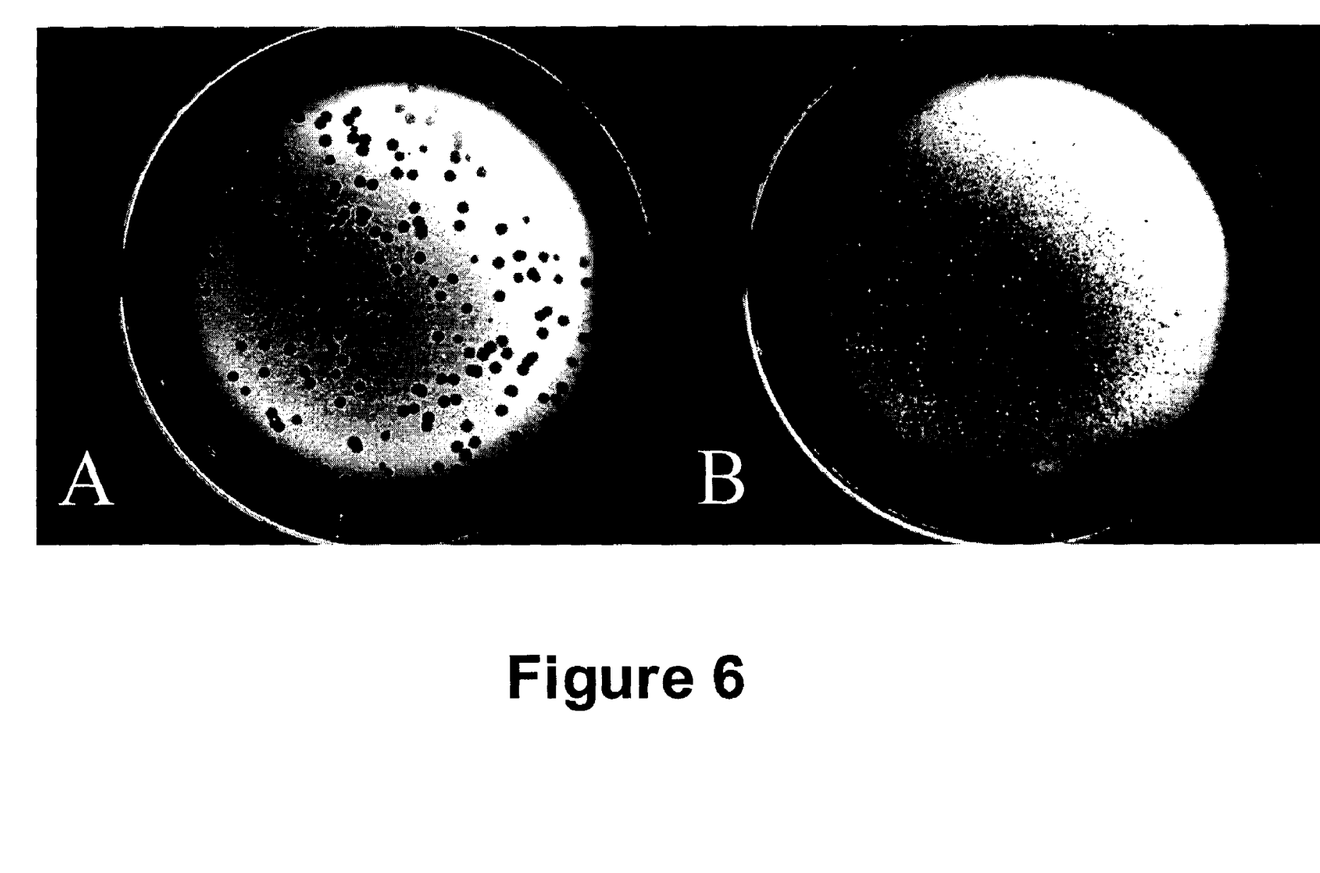
FIG. 6. Plaques of phage ö31 on (A) NCK203 (pTRKH2), $10^{-6}$ dilution; (B) NCK203 (pTRKH2:ORFY), $10^{-1}$ dilution.
Figure 7:
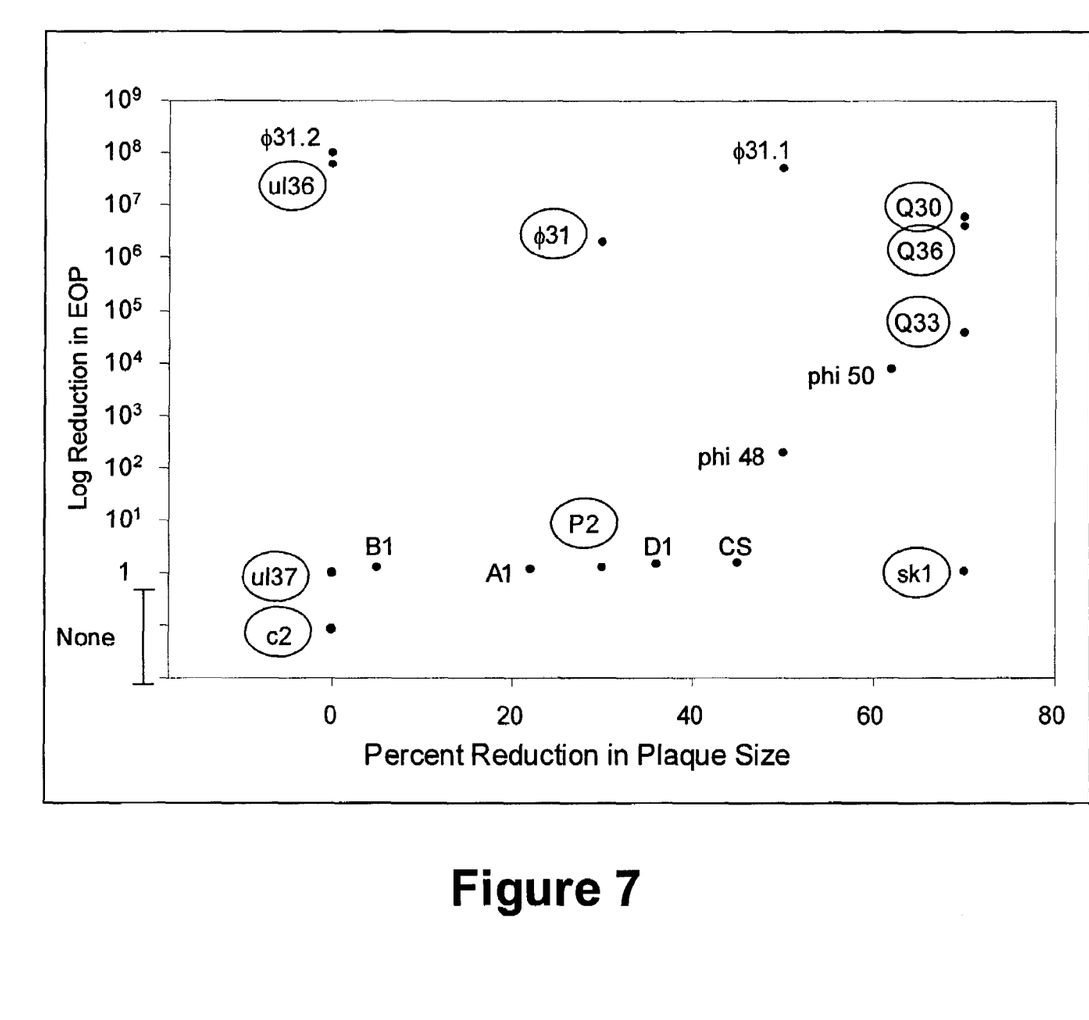
FIG. 7. Graph showing the effect of AbiZ on a prolate phage (red), two 936 species phages (green), and 14 P335 species phages (black). Phages sensitive to AbiA are circled. The EOPs of prolate phage c2 and the two 936 phages tested were not affected by AbiZ. However, plaque sizes of p2 and sk1 were reduced. All three phages are strongly inhibited by AbiA. Of the P335 phages, sensitivity to AbiZ varied from slight reductions in plaque size or EOP only, to large reductions in both. AbiA resistant phages ö31.1, ö31.2, phi 48 and phi 50 were sensitive to AbiZ. The effects of AbiA and AbiZ appear to be complimentary and will most likely have a synergistic effect on many of these phages.

The plaque size and EOP of phage ö31 were greatly reduced (FIGS. 5 and 6). Adsorption of phage ö31 was 99% to NCK203 (pTRKH2), and was 97% to NCK203 (pTRKH2:ORFY), indicating that AbiZ does not interfere with phage adsorption. Typically, Abi defenses limit the release of phage particles in phage infected cells, but the cells die due to disruption of cell functions by the infecting phage. Cell death after infection with ö31 at an MOI of 4 was 97% for NCK203 (pTRKH2) versus 90% for NCK203 (pTRKH2:ORFY), indicating an abortive phage resistance phenotype. ORF Y was designated abiZ, a new abortive infection gene from *Lactococcus lactis*.

EXAMPLE 4

The Effect of AbiZ on Lytic Lactococcal Phages of the Species P335, 936, and c2: Summary and Conclusions Plasmid pTR2030 from the naturally phage resistant starter strain *Lactococcus lactis* ME2 encodes a restriction/modification system (LlaI) and two abortive infection genes (abiA and abiZ) on a 14 kb region between two copies of IS946.

Expressed together, AbiA and AbiZ completely inhibit P335 species phage ö31.

One open reading frame on a monocistronic transcript is sufficient for AbiZ activity. Gene abiZ is expressed constitutively from its native promoter.

Abortive gene abiZ, when expressed from the high copy number shuttle vector pTRKH2, does not inhibit phage ö31 adsorption to *L. lacti* NCK203, and 90% of phage infected cells die; however the efficiency of plaquing (EOP) of ö31 is reduced to $10^{-7}$.

The EOPs of 936 group phages sk1 and p2 are not affected when abiZ is expressed in *L. lactis* MG1363, but plaque size is reduced. Prolate phage c2 is completely resistant.

Among the P335 group phages plaqued on NCK203 (pTRKH2::abiZ), various reductions in EOP and plaque sizes were observed.

The foregoing is illustrative of the present invention, and is not to be construed as limiting thereof. The invention is defined by the following claims, with equivalents of the claims to be included therein.

That which is claim is:

1. An isolated nucleic acid consisting of a nucleic acid sequence encoding a phage abortive defense protein wherein said protein consists of an amino acid sequence that is at least 95% identical to SEQ ID NO:2 .

2. The isolated nucleic acid according to claim 1 wherein the encoded phage abortive defense protein consists of the amino acid sequence set forth in SEQ ID NO:2.

3. The isolated nucleic acid according to claim 1 consisting of the sequence set forth from position 373 to position 1668 in SEQ ID NO:1.

4. An isolated nucleic acid encoding a phage abortive defense protein consisting of an amino acid sequence that is at least 95% identical to SEQ ID NO:2 operatively associated with an heterologous promoter.

5. The recombinant DNA according to claim 4, further comprising a nucleic acid sequence encoding an AbiA gene.

6. An isolated nucleic acid consisting of the nucleic acid sequence set forth in SEQ ID NO:1 which encodes a phage abortive defense protein.

7. A recombinant plasmid comprising an isolated nucleic acid according to claim 4.

8. The recombinant plasmid according to claim 7, further comprising an AbiA gene.

9. A method of imparting phage resistance to a bacteria, comprising transforming the bacteria with a nucleic acid according to any of claims 4, 5, 7, 8, or 6, thereby imparting phage resistance to said bacteria.

10. The method according to claim 9, wherein said bacteria is a *Lactococcal* bacteria.

11. The method according to claim 9, wherein said bacteria is selected from the group consisting of *Lactococcus lactis* subsp. *lactis, Lactococcus lactis* subsp. *cremoris,* and *Lactococcus lactis* subsp. *lactis biovar. diacetylactis.*

12. The method according to claim 9, further comprising introducing an AbiA gene into said bacteria.

13. A bacteria produced by the method of claim 9.

14. The bacteria of claim 13 that comprises an isolated nucleic acid encoding a phage abortive defense protein consisting of the amino acid sequence set forth in SEQ ID NO:2 operatively associated with an heterologous promoter.

15. The bacteria of claim 13 that comprises an isolated nucleic acid encoding an AbiA gene.

16. The bacteria of claim 13 that comprises a recombinant plasmid comprising an isolated nucleic acid encoding a phage abortive defense protein consisting of the amino acid sequence set forth in SEQ ID NO:2 operatively associated with an heterologous promoter.

17. A starter culture for fermenting milk comprising a Lactococcal bacteria transformed with nucleic acid according to any of claims 4, 5, 7, 8, or 6, and expresses the encoded phage abortive defense protein.

18. The starter culture according to claim 17, wherein said bacteria is selected from the group consisting of *Lactcoccus lactis* subsp. *lactis, Lactococcus lactis* subsp. *cremoris,* and *Lactococcus lactis* subsp. *lactis biovar. diacetylactis.*

19. The starter culture according to claim 17, wherein said bacteria is further transformed with an AbiA gene.

20. A method of fermenting milk, comprising
(a) transforming a Lactococcal bacteria with a nucleic acid according to any of claims 4, 5, 7, 8, or 6; and
(b) combining said transformed Lactococcal bacteria with milk under conditions that facilitate the growth of said bacteria and the expression of the nucleic acid sequence encoding the phage abortive defense protein,
thereby fermenting said milk.

21. The method according to claim 20, wherein said bacteria is selected from the group consisting of *Lactococcus lactis* subsp. *lactis*, *Lactococcus lactis* subsp. *cremoris*, and *Lactococcus lactis* subsp. *lactis biovar. diacetylactis*.

22. The method according to claim 20, wherein said bacteria is further transformed with an AbiA gene.

23. The method of claim 9, wherein said nucleic acid encodes the amino acid sequence set forth in SEQ ID NO:2.

24. The method of claim 20, wherein said nucleic acid encodes the amino acid sequence set forth in SEQ ID NO:2.

* * * * *